United States Patent
Bonnet et al.

(12)

(10) Patent No.: US 6,505,068 B2
(45) Date of Patent: Jan. 7, 2003

(54) ACTIVE IMPLANTABLE MEDICAL DEVICE, IN PARTICLUAR A PACEMAKER, DEFIBRILLATOR AND/OR CARDIOVERTOR, CAPABLE OF ELIMINATING DETECTION EVENT ARTIFACTS

(75) Inventors: Jean-Luc Bonnet, Montrouge (FR); Christine Henry, Paris (FR)

(73) Assignee: ELA Medical S.A., Montrouge (FR)

( * ) Notice: Subject to any disclaimer, the term of this patent is extended or adjusted under 35 U.S.C. 154(b) by 0 days.

(21) Appl. No.: 09/741,693

(22) Filed: Dec. 20, 2000

(65) Prior Publication Data

US 2001/0016693 A1 Aug. 23, 2001

(30) Foreign Application Priority Data

Dec. 29, 1999 (FR) ............................... 99 16634

(51) Int. Cl.$^7$ ................................. A61B 5/04
(52) U.S. Cl. ........................... 600/510; 607/27
(58) Field of Search ................ 600/510; 607/9, 607/4, 27

(56) References Cited

U.S. PATENT DOCUMENTS

| | | | |
|---|---|---|---|
| 5,193,550 A | * | 3/1993 | Duffin ..................... 600/510 |
| 5,718,242 A | | 2/1998 | McClure et al. |
| 5,891,170 A | | 4/1999 | Nitzsche et al. |
| 5,891,178 A | * | 4/1999 | Mann ..................... 607/27 |

FOREIGN PATENT DOCUMENTS

| | | | |
|---|---|---|---|
| EP | 0 334 618 | 9/1989 | .......... A61N/1/365 |
| EP | 0 813 888 | 12/1997 | .......... A61N/1/365 |

* cited by examiner

*Primary Examiner*—Angela D. Sykes
*Assistant Examiner*—Roderick Bradford
(74) *Attorney, Agent, or Firm*—Orrick, Herrington & Sutcliffe LLP

(57) ABSTRACT

An active implantable medical device, in particular a pacemaker, defibrillator and/or cardiovertor, able to identify and eliminate the artifacts of the detection of cardiac events. This device detects spontaneous events in a ventricular and/or atrial cavity cardiac; measures the intervals separating the successive detected events collected by the detection circuits; analyzes the cardiac rate of heartbeat, according to the measured values of intervals; and eliminates double detections of the same cardiac event, namely when an event detected is followed of an artifact likely to be also detected. The elimination of double detections is performed by seeking to identify an alternation of short intervals (t1, t3, t5, ...) and long intervals (t2, t4, t6, ...) in the successive measured intervals (t1, t2, t3, t4, t5, t6, ...) separating a series of consecutive events (R1, R'1, R2, R'2, R3, R'3, ...) collected by the detection circuits and, in the presence of such a proven and regular alternation, to announce that there was double detection. The elimination of double detections can in particular include statistical analysis of the distribution of the aforesaid successive intervals. The identification of the double detection is then used in the analysis of the heart rate to provide the suitable therapy as appropriate.

8 Claims, 3 Drawing Sheets

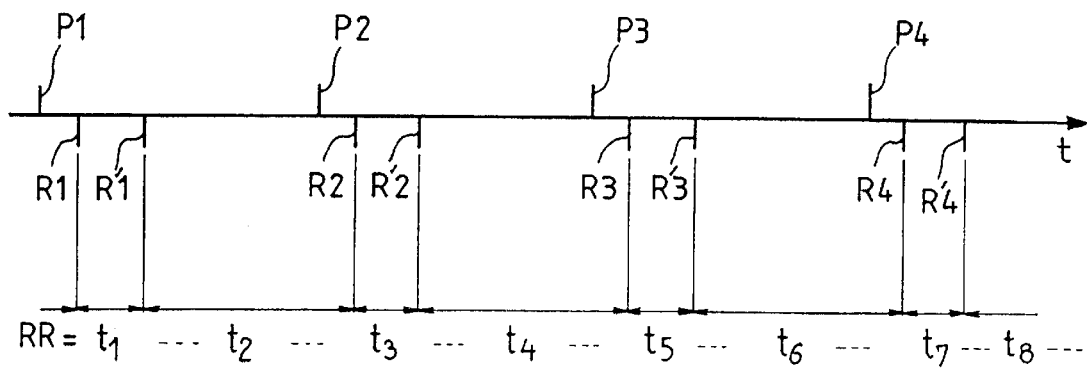
FIG_1
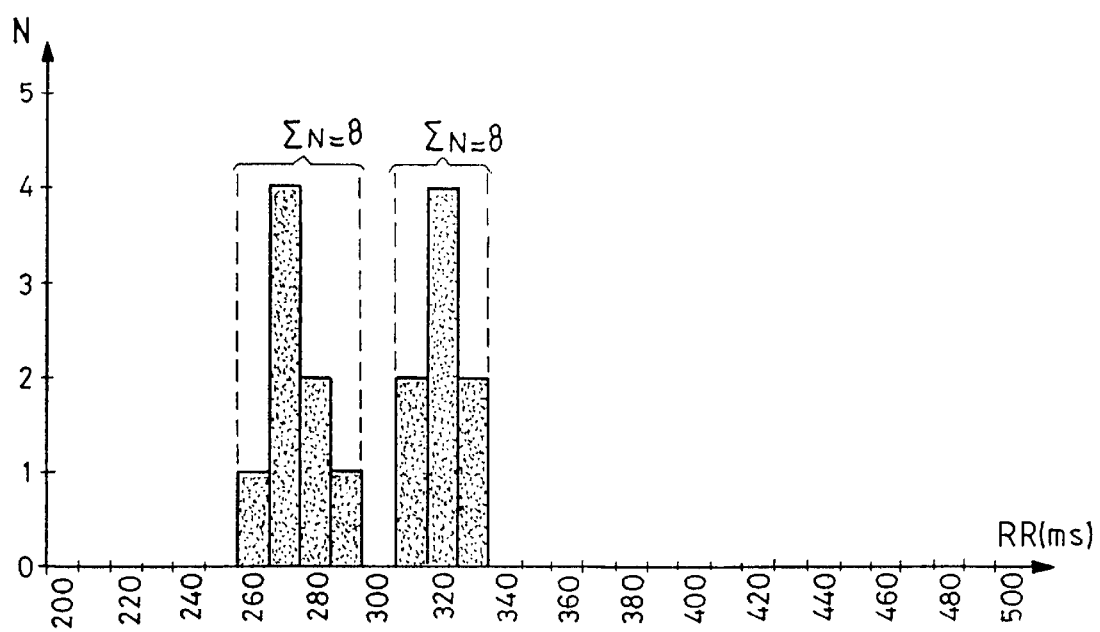
FIG_2

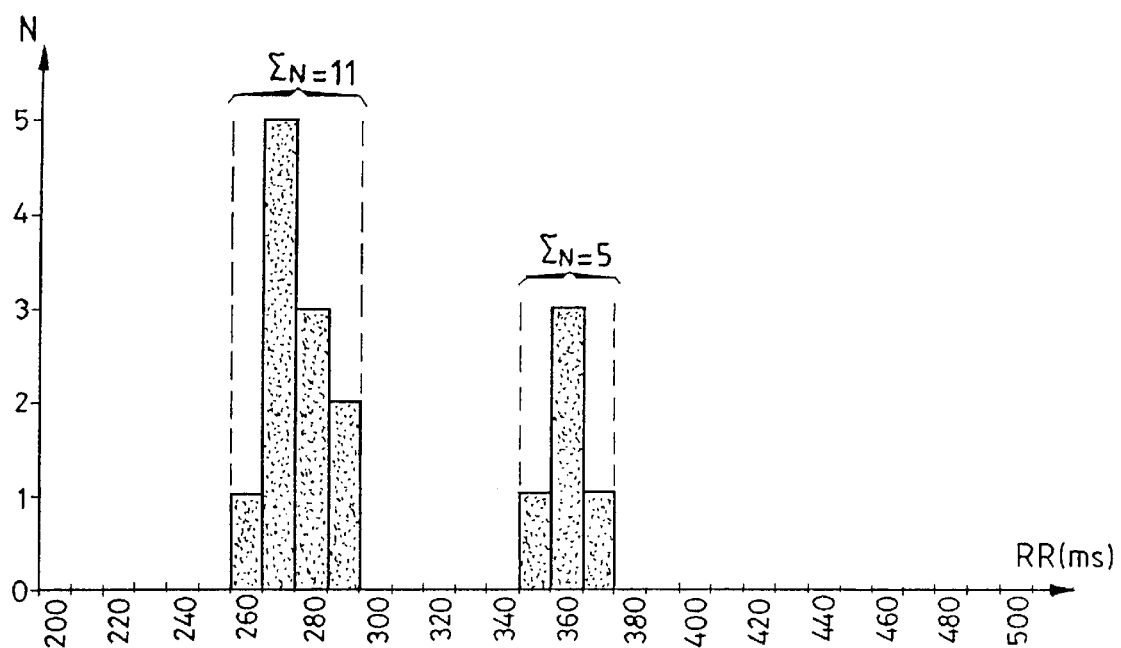
FIG_3
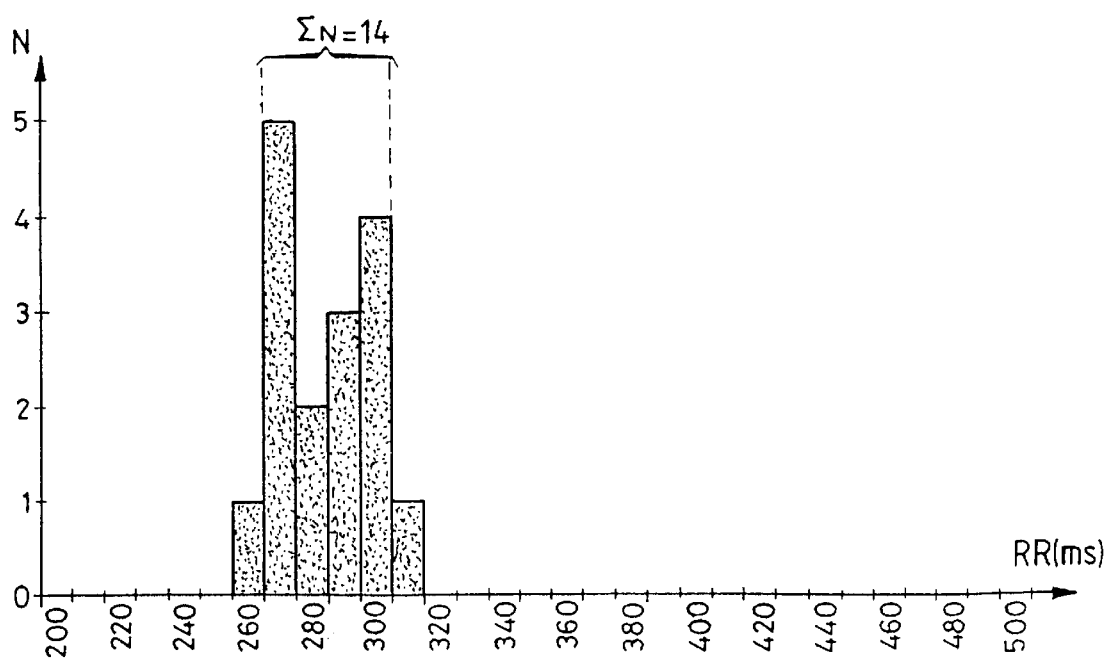
FIG_4

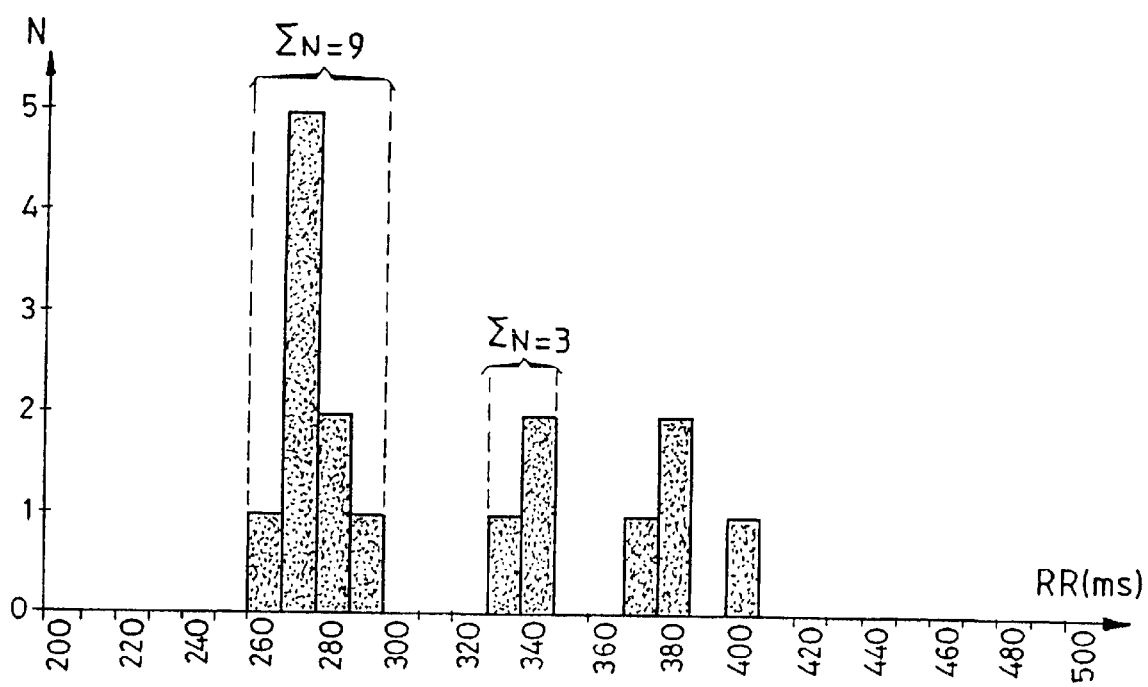
FIG_5

ACTIVE IMPLANTABLE MEDICAL DEVICE, IN PARTICLUAR A PACEMAKER, DEFIBRILLATOR AND/OR CARDIOVERTOR, CAPABLE OF ELIMINATING DETECTION EVENT ARTIFACTS

FIELD OF THE INVENTION

The present invention relates to "active implantable medical devices" as defined by the Jun. 20, 1990 directive 90/385/CEE of the Council of the European Communities, more particularly to pacemaker, "multisite" (triple or quadruple chambers), defibrillator and/or cardiovertor devices, each of whose operation depends upon the detection of cardiac signals spontaneously produced by the heart of the patient bearing the device, to record data, to pose a diagnosis or to apply a suitable therapy, as the case may be.

BACKGROUND OF THE INVENTION

It is essential that the behavior of the active implantable medical device respects the physiology of the patient or, at the very least, does not create any harm for the patient. One difficulty encountered in this respect lies in the problem of over-detection of the cardiac activity, i.e., situations where the device detects not only a cardiac event itself (e.g., the depolarization wave of the cardiac cavity being considered), but also an artifact associated with that same event, and wrongly considers the artifact as another event which has occurred after the one just detected.

These artifacts can be of various origins. Thus, when the spontaneous cardiac event presents several components of which some occur tardily after other components which produce a detection of the event, for example, the repolarization wave or T-wave follows the depolarization wave or QRS wave complex and can be detected, wrongly, as a new spontaneous vent distinct from the preceding spontaneous event based on detection of the QRS complex.

The same issue exists for the "cross talk," which is a detection in one cavity of an activity, whether a stimulation or a detection event, coming from another cavity, generally, for example, the detection in the atrial cavity of a ventricular event (depolarization or repolarization).

Various techniques have been proposed to mitigate the risks of over-detection. One technique is the application of a filtering function, analog or digital, in order to eliminate the fast components from the repolarization signal. Another technique is the application of refractory periods, for use in the same cavity or between cavities. Yet another technique is the automatic adjustment of the sensitivity of the detection amplifiers, or the automatic adjustment of the gain of these amplifiers.

However, the use of these various techniques is always done to the detriment of a good detection, principally if there is no over-detection. As an example, long refractory periods provide protection of the device against inopportune detections, but they reduce the sensing capacity of the system and are likely to lead to "false negatives" if they are too long and let an event pass without detecting it. In the same way, in order to ensure the detection of a ventricular fibrillation ("VF"), the amplitude of such a signal being low, it is necessary to seek a maximum sensitivity in order to detect those events which should be detected.

There are also risks of making "false positive" detections, in particular in the case of certain particularly long endocardiac signals. This problem generally concerns patients presenting dilated cardiopathies for which the duration of depolarization, mainly ventricular, is then increased.

The analysis of the time intervals separating detected successive events (e.g., RR intervals in the case of the ventricular events) is realized in various diagnosis algorithms inside pacemakers, as the one which is described, for example, in the EP-A-0 626 182 and its counterpart U.S. Pat. No. 5,462,060 (both commonly assigned herewith to Ela Médical). Double detections are obviously likely to deceive this type of algorithm and to lead to sub-optimal actions of the pacemaker (here and in the following discussion, one will understand the term "pacemaker" to refer to the pulse generator on its own or as a component of a defibrillator or cardiovertor).

Thus, for a patient presenting a normal sinusal heartbeat rate, the presence of double detections would result in a determination of an average rate as being at a level that is much higher than the real rate. In such a case, there is a risk of application of an undesirable antitachycardic therapy (e.g., a cardioversion shock or a defibrillation shock) in the case of a cardiovertor/defibrillator. The application of the foregoing means would have as a consequence a risk of non-diagnosis of the VF.

The known protection systems described above are not adequately capable of protecting the device against a double detection from the same cardiac event.

OBJECTS AND SUMMARY OF THE INVENTION

It is, therefore, an object of the present invention to minimize risk of double detection, by means applicable in particular to the typical situations described above, without reducing the sensing capacity of the device.

The starting point of the invention lies in the observation by the inventors that on the one hand, the doublet wave detected resulting from a "double detection" (i.e., the detection of an event and an artifact related to the event), is wrongly considered by the device as a succession of two distinct events, generally takes place prematurely in the cardiac cycle, and on the other hand, the interval of time separating two successive doublets is longer than the one separating the two detections of the doublet. Stated in other words, the event-artifact interval is shorter than the following artifact-event interval.

This situation of an erroneous "double detection" differs from the situation of arrhythmia, where the intervals are generally short and stable for tachycardias, and unstable for fibrillations. Those arrhythmia situations are revealed by detections of frequently occurring events, which are not to be confused with double detections.

The guiding principle underlying the invention then is the recognition of the short interval/long interval alternation. This alternation reveals the presence of a double detection. This phenomenon can then be taken into account during the analysis of the detected signal, in particular by the means for analyzing the signals which determines the cardiac rate from successive detections.

Thus, if one designates the letter L to represent a long cycle corresponding to the normal sinusal coupling (i.e., the time by which a ventricular event follows an atrial event under normal conditions), the letter C to represent a short cycle (typically due to an artifact) and the letter M to represent a cycle of intermediate duration intervening after a cycle C, one obtains the following relations in the case of the erroneous detection of a late occurring signal:

duration L≈duration C+duration M
number of C cycles=number of M cycles
a C cycle is always followed by an M cycle (a "CM" pattern)

One standard sequence describing a phenomenon of late detection over a number of cycles could be: L L L C M C M C M C M L L.

Broadly, the present invention is directed to an implantable medical device of the known type including: means for detecting spontaneous events in a cardiac cavity, including a ventricular or an atrial cavity; means for measuring the intervals separating the successive events collected by the detection means; means for analyzing the cardiac rate, operating-according to the values of intervals thus measured; and means for eliminating double detections of the same event, when an event is followed by an artifact also likely to be collected by the means of detection.

According to the invention, the elimination means is capable of identifying an alternation of short intervals and long intervals in the successive intervals separating a series of consecutive events collected by the detection means and, in the presence of such a proven and regular alternation, to announce or indicate to the analysis means that there was a double detection. The analysis means can then take steps to eliminate the tardy detection event and thus treat the double detection as a single event for purposes of its operation.

In a preferred embodiment, the elimination means includes means for performing a statistical analysis of the distribution of the values of the aforesaid successive intervals. Such a statistical analysis means can in particular include: means for classifying the successive intervals according to the length of the interval, distributing the intervals in a histogram comprising a plurality of classes corresponding to consecutive ranges of interval values; and means for determining, starting from the number of intervals classified in each range, the presence of two statistically equivalent peaks in the histogram and, in such a case, to consider that there was double detection.

In one preferred implementation, the statistical, analysis means operates to determine that there is a presence of two statistically equivalent peaks only if: (1) the two peaks are distinct, for example, separated by at least one empty class; (2) there is a principal peak which gathers more than some percentage, e.g., 40%, of the total number of the intervals; and (3) there is a secondary peak which gathers about as many, if not the same number of, intervals as the principal peak.

An additional criterion which can be employed to discriminate double detections is to evaluate the duration C of the short cycles, the duration L of the long cycles and the duration M of the intermediate cycles, and to announce to the means for analyzing the heartbeat rate that there was double detection if: L≈C+M.

BRIEF DESCRIPTION OF THE DRAWINGS

Other characteristics, features and advantages of the present invention will appear to a person of ordinary skill in the art in view of the following detailed description, made with reference to the annexed drawings, in which like reference characters refer to like elements, and in which:

FIG. 1 is a chronogram showing a succession of cardiac events collected on the atrial and ventricular channels of detection, in a situation of double detection, over time t;

FIG. 2 is a histogram of RR intervals in a situation of proven double detection; and FIGS. 3 to 5 are histograms of RR intervals corresponding to situations in which it is not possible to conclude that there is a presence of a double detection situation.

DETAILED DESCRIPTION OF THE DRAWINGS

Referring to FIG. 1, a chronogram of detected cardiac signals in the typical case of a double detection are shown over time t, with detected atrial events indicated by a P and detected ventricular events indicated by an R.

The well-known PQRST wave complex corresponding to a cardiac depolarization results in an atrial detection designated as a P-wave (P1, P2, P3 . . . ), followed by a ventricular detection, designated as the R-wave of the QRS component (R1, R2, R3 . . . ).

In the case of a double detection, a ventricular detection R1, R2, R3 . . . is followed by a "false" detection R'1, R'2, R'3 . . . constituting an artifact. This false detection can in particular be caused by a residual T-wave signal remaining after conventional filtering of the collected signal, or by a systemic extrasystole on a ventricular depolarization (a situation called "bigeminism," which is a situation in which the application of a therapy is not required). In a characteristic manner, intervals R1–R'1, R2–R–'2, R3–R'3 . . . separating the true detection from the artifact for the same cardiac cycle are relatively stable, about 200 ms.

On the other hand, the intervals R'1–R2, R'2–R3 . . . separating the artifact of the detection from the following cardiac cycle can be rather variable and are not foreseeable, because they depend in fact on the sinusal rhythm of the patient. These intervals can typically vary from 400 ms (with patient effort) to 800 ms (at rest), but they are always longer than intervals R1–R'1, R2–R'2, R3–R'3 . . . and this, to a significant degree. It is such a situation that, according to the invention, the device will try to detect in order to recognize a situation of double detection.

One will take the hypothesis that a double detection (presence of R and R' on the same cardiac cycle) is almost permanently present, i.e., where this situation exists, for example, on 80% of the cardiac cycles; in the contrary case, if it would be the sporadic appearance of double detections, the consequences of such double detections would be strongly minimized by the averaging effect accomplished by the algorithm over a number of cardiac cycles, and the stability analysis of the intervals, without it even being necessary to carry out an additional discrimination.

The device in accordance with the present invention is implemented, in a way in itself known:

means for detecting atrial and/or ventricular cardiac events, for example, the ventricular events R1, R'1, R2, R'2, R3, R'3, R4, R'4 . . . in the illustrated example, having at least a ventricular lead, and circuits for the amplification and filtering of the signal collected by this lead, and further includes circuits able to measure intervals of times $t_1, t_2, t_3, t_3, t_4, t_5$ . . . between each two successively detected activity events, and means for classifying the measured cardiac intervals, typically in the form of histograms such as those illustrated on FIGS. 2 to 5.

These detecting and classifying means are in particular present in the "PARAD" algorithm for diagnosis of the arrhythmias (PARAD is a trademark of ELA Médical), which is a diagnosis algorithm used in commercial devices such as the DEFENDER or ALTO model defibrillators of ELA Médical, which algorithm is in particular the subject of application EP-A-0 626 182 and U.S. Pat. No. 5,462,060 cited above. It also should be understood that any circuit structure suitable for detecting the cardiac events and their relative times and intervals may be used and the inventions not at all limited to the structure of the DEFENDER or ALTO defibrillators.

The classification of the measured cardiac intervals in accordance with the present invention distributes the intervals in a certain number of classes or ranges corresponding to consecutive joined intervals and preferably having the same width, typically 10 ms. All the intervals have the same weight in the histogram (unit weight), and the histogram preserves only a certain predetermined number of consecutive intervals, typically the last 16 intervals. With each cycle, the oldest interval in the histogram is withdrawn and the most recent interval is then included. The histogram is thus updated at each cycle and contains the analysis of the distribution of the last sixteen measured cardiac intervals. It should be understood, however, that the specifics of the foregoing embodiment, e.g., number of cycles, number and width of classes, and weighting, could be modified as may be appropriate in a given circumstance.

In view of a simplification of the invention, one can filter the intervals for which the duration is higher than a given threshold (known as the "cut-off rate" or the Tachycardia Detection Interval ("TDI")). In the contrary case, one will be able to envisage an additional selection criterion, by retaining for analysis of double detections only the cycles for which the following relation is satisfied: duration L≈duration C+duration M (C indicating the short cycles, L the long cycles and M the cycles of intermediate duration).

From the histograms thus generated (of which various examples are illustrated on FIGS. 2 to 5), the device seeks to identify the presence of one or more peaks. The device thus operates to calculate the amplitude of a series of classes, typically a series formed of the sum of a number of consecutive classes, and seeks the series presenting the largest sum ΣN starting from the left (i.e., starting from the class of the shortest intervals), which series which will be defined as being the "principal peak".

With reference to the example shown in FIG. 2, the principal peak is the peak on the left side, corresponding to a series of four consecutive classes 260–270 ms, 270–280 ms, 280–290 ms and 290–300 ms, gathering a total number of detections N to be ΣN=8 detections.

The system then seeks, in the same manner, to identify another peak, which will be called the "secondary peak". For the example shown on FIG. 2, this secondary peak corresponds to the peak on the right-hand side, which gathers the relatively longer intervals in a series of three consecutive classes, 310–320 ms, 320–330 ms and 330–340 ms, also for a total ΣN=8 detections.

As it easily will be understood by a person of ordinary skill in the art, in the case of a stable and proven double detection corresponding to the chronogram of FIG. 1, the principal peak corresponds to the short intervals $t_1, t_3, t_5, \ldots$ while the secondary peak corresponds to the long intervals $t_2, t_4, t_6 \ldots$ The system then checks if the principal peak and the secondary peak are "equivalent", i.e., if they fulfill certain criteria. If the two peaks are deemed to be equivalent, the device then considers that a stable double detection is well installed in the patient. This phenomenon is announced to the rate analyses means for taking it into account for further calculations, for example, in calculating the heartbeat rate.

In a preferred embodiment, the following criteria are used to determine whether or not the two peaks are equivalent. A first condition to satisfy in determining that the two peaks, the principal and secondary peaks, are equivalent is that the principal peak gathers more than 40% of the detected intervals. This first condition is satisfied in the case of the histogram of FIG. 2, and also in the histograms of FIGS. 3 and 5, but not in the case of the histogram of FIG. 4.

A second condition to be satisfied so that the two peaks can be regarded as equivalents is that those peaks are disjoined peaks, i.e., they are separated by at least one empty class between the two series of consecutive values comprising each peak. This condition is satisfied on the histograms of FIGS. 2 and 3. It is not satisfied in the histogram of FIG. 4, where one does not find two distinct peaks, but only one peak gathering a very large majority of the intervals (in the example of FIG. 4, fourteen out of sixteen intervals).

The situation where the two peaks are not disjoined most probably corresponds to a tachycardia, which will have to be diagnosed and confirmed by other criteria not pertinent to the present invention.

A third condition to be satisfied is that the secondary peak gathers as many cycles as the principal peak. This is the case on the example of histogram of FIG. 2, where the secondary peak gathers eight intervals out of the sixteen. This is not the case, however, on the histograms of FIGS. 3 and 5, although in those histograms the first two mentioned conditions are fulfilled. This last situation probably corresponds to an atrial fibrillation, which could however be diagnosed and confirmed by an analysis based on other criteria, also not pertinent to the present invention.

In all of these cases, if the device cannot show the presence of a stable double detection, i.e., if one at least of the three conditions above is not respected, the device continues its analysis on the basis of other criterion, such as those described for example in the aforementioned EP-A-0 626 182 and U.S. Pat. No. 5,462,060 or the EP-A-0 838 235, (and its corresponding U.S. Pat. No. 5,868,793) which describe various rate analysis processes based mainly on the analysis of the stability and the evolution of RR and PR intervals.

In an alternate embodiment, one may add a criterion on the position of the first peak (i.e., the one gathering the shortest intervals, thus corresponding to intervals R1–R'1, R2–R'2 . . . ) to refine the diagnosis in the event of a proven double detection: if the corresponding values are higher than a limiting value, then it is probably a double detection resulting from a ventricular extrasystole (bigeminism); in the contrary case, short RR' intervals reveal the detection of a residue of the T wave notwithstanding the filtering which may have been applied.

It will be appreciated that the present invention is preferably implemented by use of software instructions in a microprocessor controlled active implantable device having sufficient memory for analyzing the cardiac signals, creating the histograms, and analyzing the histograms. It also should be understood that any circuits capable of performing the stated functions, whether microprocessor controlled, digital logic, analog circuits; or a combination of the foregoing, may be used as known to a person of ordinary skill in the art. Advantageously, software for implementing the present invention can be downloaded by telemetry transmission to an already implanted microprocessor controlled device to update the operation of such a device. Similarly, the compiled histogram data preferably, can be uploaded to a remote programmer for analysis by a clinician.

One skilled in the art will appreciate that the present invention can be practiced by other than the described embodiments, which are presented for the purposes of illustration and not of limitation.

We claim:

1. An active implantable medical device, comprising:
   means for detecting spontaneous events in a ventricular or atrial cardiac cavity;
   means for measuring an interval separating successive detected events;

means for analyzing a heartbeat rate, according to said measured intervals; and means for eliminating double detection of a detected event comprising means for evaluating successive measured intervals (t1, t2, t3, t4, t5, t6, ... ) separating a series of consecutive detected events (R1, R'1, R2, R'2, R3, R'3, ... ), and identifying therefrom a short interval and a long interval and an alternation of short intervals (t1, t3, t5, ... ) and long intervals (t2, t4, t6, ... ) in said successive intervals as a double detection corresponding to a detected spontaneous event followed by a detected artifact.

2. The device of claim 1, wherein the means for elimination of double detections further comprises means for statistically analyzing a distribution of said successive measured intervals.

3. The device of claim 2, wherein the statistical analysis means comprises:

means for classifying said measured intervals and distributing said successive measured intervals in a histogram comprising a plurality of classes corresponding to ranges of consecutive values of intervals, and means for counting a number of measured intervals classified in each range, determining from said histogram a principal peak and secondary peak that are equivalent statistically and correspond to said double detection.

4. The device of claim 3, wherein the statistical analysis means operates to determine that there is a presence of two statistically equivalent peaks only if said principal peak is distinct from said secondary peak.

5. The device of claim 4, wherein the statistical analysis means operates to determine that the principal and secondary peaks are distinct if they are separated by at least one class in said histogram having no measured intervals in said one class.

6. The device of claim 3, wherein the statistical analysis means operates to determine that the principal and secondary peaks are statistically equivalent only if the principal peak count is more than 40% of the total count of the intervals in said histogram.

7. The device of claim 3, wherein the statistical analysis means operates to determine that the principal and secondary peaks are statistically equivalent only if the secondary peak count of intervals is as great as the principal peak count of intervals.

8. The device of claim 1, wherein the elimination means further comprises means for evaluating a length of the measured intervals and identifying a duration C corresponding to a short cycle length, a duration L corresponding to a long cycle length and a duration M corresponding to an intermediate cycle length, and for determining that there is said double detection if L~C+M.

* * * * *

UNITED STATES PATENT AND TRADEMARK OFFICE
CERTIFICATE OF CORRECTION

PATENT NO. : 6,505,068 B2
DATED : January 7, 2003
INVENTOR(S) : Jean-Luc Bonnet and Christine Henry It is certified that error appears in the above-identified patent and that said Letters Patent is hereby corrected as shown below:

Title page, Item [54] and Column 1, line 2,
After "IN" delete "PARTICLUAR" and insert -- PARTICULAR --;

Title page,
Item [57], ABSTRACT,
Lines 4-5, after "atrial" delete "cavity cardiac" and insert -- cardiac cavity --;
Line 10, after "followed" delete "of" and insert -- by --;

Column 3,
Line 14, after "operating" delete "—"
Line 38, after "statistical" delete ","

Column 4,
Line 1, delete "DRAWINGS" and insert -- INVENTION --
Lines 14-15, after "can" insert -- , --; and after "particular" insert -- , --

Column 6,
Lines 15-16, after "case" delete "on" and insert -- in --; and before "histogram" insert -- the --;
Line 20, after "could" and "however" respectively insert -- , --;
Line 24, after "if" delete "one" and after "least" insert -- one --
Lines 26-27, after "other" delete "criterion" and insert -- criteria --; after "described" and "example" respectively, insert -- , --
Line 50, after "circuits" delete ";" and insert -- , --;
Line 56, after "preferably" delete ",";

UNITED STATES PATENT AND TRADEMARK OFFICE
CERTIFICATE OF CORRECTION

PATENT NO.    : 6,505,068 B2
DATED         : January 7, 2003
INVENTOR(S)   : Jean-Luc Bonnet and Christine Henry It is certified that error appears in the above-identified patent and that said Letters Patent is hereby corrected as shown below:

Column 8,
Line 26, after "L" delete "~" and insert -- ~~ --

Signed and Sealed this

Twenty-eighth Day of December, 2004

JON W. DUDAS
*Director of the United States Patent and Trademark Office*